(12) United States Patent
Bernard et al.

(10) Patent No.: US 8,406,475 B2
(45) Date of Patent: Mar. 26, 2013

(54) METHOD AND DEVICE FOR ANALYZING BERRIES

(75) Inventors: Nicolas Bernard, Pignan (FR); Boris Larcheveque, Bezouce (FR); Olivier Bertrand Daniel Zebic, La Boissiere (FR)

(73) Assignee: D.Wine, Aire sur l'Adour (FR)

( * ) Notice: Subject to any disclaimer, the term of this patent is extended or adjusted under 35 U.S.C. 154(b) by 1282 days.

(21) Appl. No.: 11/994,120

(22) PCT Filed: Jun. 29, 2006

(86) PCT No.: PCT/FR2006/001513
§ 371 (c)(1),
(2), (4) Date: Jan. 31, 2008

(87) PCT Pub. No.: WO2007/003763
PCT Pub. Date: Jan. 11, 2007

(65) Prior Publication Data
US 2010/0215221 A1 Aug. 26, 2010

(30) Foreign Application Priority Data
Jun. 30, 2005 (FR) ...................................... 05 06742

(51) Int. Cl.
*G06K 9/00* (2006.01)
*G06K 9/34* (2006.01)
*G06K 9/46* (2006.01)
*G06K 9/66* (2006.01)

(52) U.S. Cl. ........ 382/110; 382/164; 382/165; 382/190; 382/191; 382/203

(58) Field of Classification Search .................... None
See application file for complete search history.

(56) References Cited

U.S. PATENT DOCUMENTS
5,546,475 A * 8/1996 Bolle et al. .................... 382/190

FOREIGN PATENT DOCUMENTS
| EP | 0 685 814 | 12/1995 |
|---|---|---|
| JP | 04238252 | 8/1992 |
| JP | 04294259 | 10/1992 |

(Continued)

OTHER PUBLICATIONS

Herrera et al., "Shortwave-near infrared spectroscopy for non-destructive determination of maturity of wine grapes", Inst. of Physics Pub., Measurement Science and Technology, 14, 2003, pp. 689-697.*

(Continued)

*Primary Examiner* — Tom Y Lu
*Assistant Examiner* — Thomas Conway
(74) *Attorney, Agent, or Firm* — Young & Thompson

(57) ABSTRACT

Method for analyzing berries, characterized in that: berries are arranged on an analysis plate, an image of the berries is recorded, the image consisting of pixels of at least one component of an elementary color, the contours of the berries are identified, and geometric and/or colorimetric characteristics of the berries are determined. The number of berries can then be determined, or a volume, a surface area, a surface area to volume ratio, and a characteristic concentration for each berry can be determined, in addition to an average, for all of the pixels inside the contour of a defined berry, of the values of a component of an elementary color of a component of interest. A device for implementing the method is also disclosed. The invention especially relates to viticulture and to the analysis of the maturity of the grape.

39 Claims, 6 Drawing Sheets

FOREIGN PATENT DOCUMENTS

WO     WO 01/37131     5/2001

OTHER PUBLICATIONS

Figure 1A:
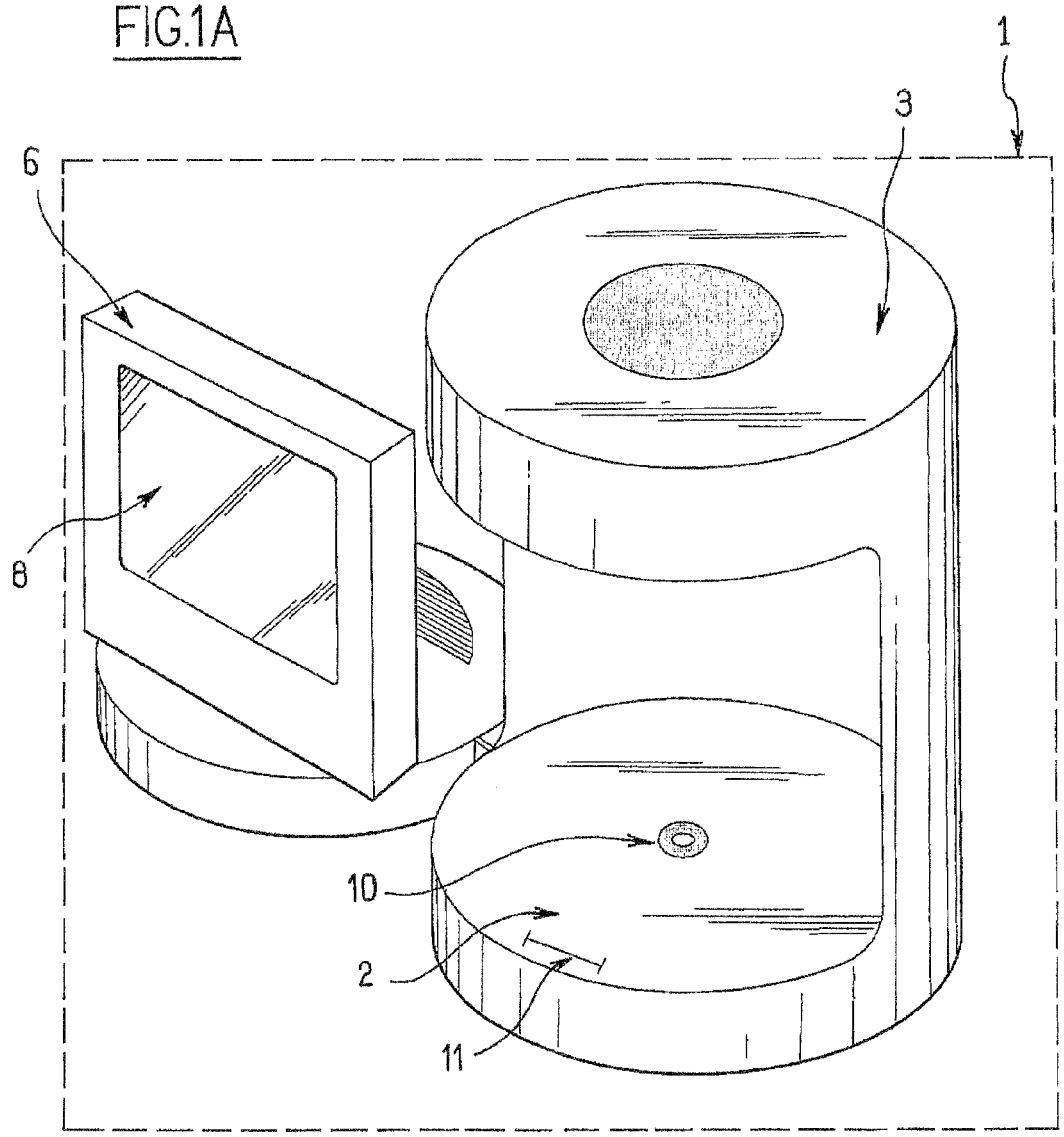

Mehl et al.; "Development of hyperspectral imaging technique for the detection of apple surface defects and contaminations"; Journal of Food Engineering vol. 61, Issue 1, Jan. 2004, pp. 67-81.*

J. Herrerra et al. "Shortwave-near infrared spectroscopy for non-destructive determination of maturity of wine grapes", Institute of Physics Publishing, Measurement Science and Technology vol. 14 (Apr. 15, 2003) pp. 689-697. Online at stacks.iop.org/MST/14/689.

Australian Office Action Patent Application No. 2006264799, dated Feb. 8, 2011.

Feng, G. et al., "Study on color image processing based intelligent fruit sorting system" Intelligent Control and Automation, 2004. WCICA 2004. Fifth World Congress on Hangzhou, China Jun. 15-19, 2004, , vol. 6, Jun. 15, 2004 pp. 4802-4805.

Gejima, Y. et al., "Judgment on level of maturity for tomato quality using l a b color image processing" Advanced Intelligent Mechatronics, 2003. AIM 2003 Proceedings 2003 IEEE/ASME International Conference on Jul. 20-24, 2003, vol. 2, Jul. 20, 2003 pp. 1355-1359.

Pla, F. et al., "An integral automation of industrial fruit and vegetable sorting by machine vision" ETFA 2001. 8th International Conference on Emerging Technologies and Factory Automation, Proceedings IEEE, vol. 2, 2001 pp. 541-546.

Polder, G. et al., "Tomato sorting using independent component analysis on spectral images" Real-Time Imaging, Academic Press Limited, GB. vol. 9, No. 4, Aug. 2003, pp. 253-259.

Rosenberger, C. et al., "Calibration and quality control of cherries by artificial vision" Journal of Electronic Imaging SPIE-INT Soc. Opt. Eng USA, vol. 13, No. 3, Jul. 2004, pp. 539-546.

\* cited by examiner

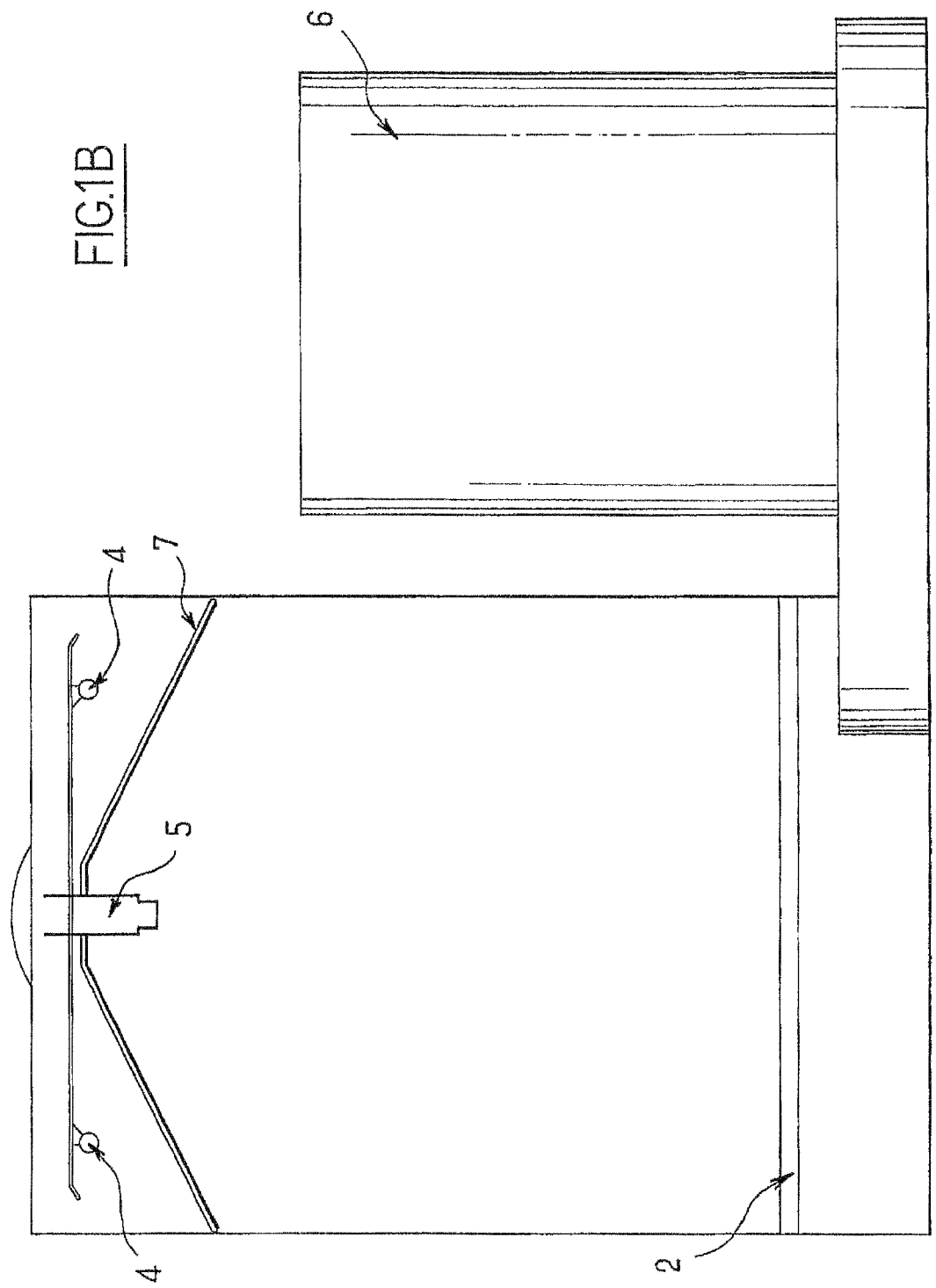

METHOD AND DEVICE FOR ANALYZING BERRIES

TECHNICAL FIELD

The present invention relates to a method for analyzing berries. It also relates to a device for analyzing berries implementing this method.

Analysis of berries makes it possible in particular to assess their maturity and heterogeneity. The field of the invention is more particularly that of viticulture and analysis of the maturity of the grape.

STATE OF THE ART

It is essential, for a good wine-making process, to determine the optimum maturity of the grape.

Maturation is a complex phenomenon, involving biosyntheses, transports, storages and conversions of different elements such as sugars and organic acids, phenols or flavour precursors. Numerous techniques now make it possible to assess the maturity of the grape.

For example, techniques such as the measurement of the concentration of sugars or acids of grape berries by chemical assay can be mentioned. The sugar-acid ratio, called the maturation index, does not make it possible to affirmably conclude on the maturity of grape berries, it is also necessary to be concerned with the values of the two components of this ratio, and consider this ratio on a scale which is specific to each variety of vine.

There can also be mentioned techniques such as tasting berries, which is subjective in character and limited as regards sampling, or studying the ratio of the concentration of tartaric acid to malic acid.

All these techniques do not make it possible to fully ascertain the maturity of the grape, nor to monitor the maturation in its complexity.

The purpose of the present invention is to propose a method and a device for analyzing berries, in particular grape berries, not starting with chemical assays, but with visual characteristics of berries. The advantage of monitoring a visual characteristic such as the volume of the berries is that it makes it possible directly to trace volume kinetics of berries, and thus makes it possible to foresee or notice for example wilting of the berries.

DISCLOSURE OF THE INVENTION

This objective is achieved with a method for analyzing berries, characterized in that it comprises:
 arranging berries on an analysis plate,
 an acquisition of an image of the arranged berries, said image of the berries being composed of pixels of at least one elementary colour component,
 an identification of contours of the berries, and
 a determination of geometric and/or colorimetric characteristics of the berries.

The method according to the invention can also comprise lighting the berries according to predetermined lighting conditions.

The method according to the invention can also comprise a geometric calibration of the image of the berries, or a correction of the colours of the image of the berries.

The identification of the contours of the berries can comprise:
 a conversion of the image of the berries to a thresholded image, in which blocks of berries can be distinguished,
 a deletion of impurities from the thresholded image, and
 a segmentation of the blocks of berries into berries with defined contours.

The conversion to a thresholded image can comprise a thresholding of the image of the berries according to a threshold for a value of an elementary colour component.

The deletion of impurities can comprise a succession of erosions and dilations of the blocks of berries or an algorithm for filling holes by propagation.

The segmentation of the blocks of berries can comprise:
 a conversion of the thresholded image to a grey-scale image,
 a thresholding of the grey-scale image by fuzzy logic,
 a use of an erosion operator until a centre of gravity is obtained for each berry, and
 an expansion around the centres of gravity, until the contours of the berries are obtained.

The method according to the invention can also comprise a determination of the number of berries in the image of berries.

The determination of characteristics can comprise a determination of a volume per berry, as well as an average and a heterogeneity factor of the volume of all the berries. The determination of characteristics can also comprise a determination of surface area per berry, as well as an average and a heterogeneity factor of the surface area of all the berries. The determination of characteristics can also comprise a determination of a surface area to volume ratio per berry, as well as of an average and a heterogeneity factor of the surface area to volume ratio of all the berries. This determination of characteristics can also comprise, for each berry and at least one elementary colour component, a calculation of an average, for all the pixels of the image of the berries inside the contour of a considered berry, of the values of a considered elementary colour component. In the case where the elementary colour component is situated in the infrared, the method according to the invention can also comprise a determination, by infrared spectrophotometry and chemometry, of at least one characteristic concentration per berry, as well as a determination of an average and a heterogeneity factor of at least one of the characteristic concentrations of all the berries. The characteristic concentrations can for example consist of a quantity of sugar, an acidity, a nitrogen concentration, an anthocyanin concentration, or a polyphenol concentration. Moreover, this determination of characteristics can also comprise, for each berry and at least one colour component of interest, a calculation of an average, for all the pixels of the image of the berries inside the contour of a considered berry, of the values of a considered colour component of interest, from the averages of values of an elementary colour component. Finally, this determination of characteristics can also comprise a calculation of an average and a heterogeneity factor of the averages of the values of an elementary colour component or a colour component of interest of all the berries. By heterogeneity factor can be meant a dispersion coefficient calculated by a standard deviation to average ratio.

In a first embodiment applied to white grape berries, the colour components of interest can be yellow and green.

In a second embodiment applied to red grape berries, the colour components of interest can be red and black.

The method according to the invention can also comprise the step of accessing to a database comprising in particular other results of berry analyses obtained using any method. These analysis results can therefore be both geometric and/or colorimetric characteristics obtained using a method according to the invention, and other types of data such as concentrations per berry, such as the acidity as well as the sugar assay, which, coupled with the volume gives the sugar content level.

The method according to the invention can also comprise a visualization of the determined geometric and/or colorimetric characteristics and/or of other data. It can also comprise a visualization of a development over time of geometric and/or colorimetric characteristics determined according to the invention and/or of other data. Among the examples of other data, there can be mentioned data originating from a database or any other source.

It can also comprise an export, to a spreadsheet file, of the geometric and/or colorimetric characteristics, and/or other results of berry analysis obtained using any method. In a preferential embodiment, the file is an Excel file.

The method according to the invention can also comprise a reiteration of the method according to the invention on the same type of berries. The method according to the invention can then also comprise an analysis over time of the geometric and colorimetric characteristics of the berries.

According to another aspect of the invention, a device for analyzing berries is proposed, implementing the above method, characterized in that it comprises:
an analysis plate,
means for acquiring an image of berries arranged on the analysis plate, said image being composed of pixels of at least one elementary colour component, and
means for determining geometric and/or colorimetric characteristics of the berries.

The device according to the invention can also comprise means for lighting berries arranged on the analysis plate. It can then also comprise a ground glass surface situated between the lighting means and the analysis plate, and situated upstream of the means for acquiring an image of the berries. In this manner, the lighting of the analysis plate is more homogeneous, and the means for acquiring an image do not see through the ground glass.

The analysis plate can be of a colour distinct from the colour of the berries.

The analysis plate can comprise spaced recesses.

The means for acquiring an image of berries can comprise a digital imaging device possessing pixels of three elementary colour components: red, green, and blue. It would also be possible to envisage a multispectral camera making an acquisition of an image of berries in a visible range and/or an infrared range, to allow in addition the direct acquisition of a characteristic concentration such as a quantity of sugar, an acidity, a nitrogen concentration, an anthocyanin concentration, or a polyphenol concentration.

The device according to the invention can also comprise means for geometrically calibrating the image of berries. These means for geometrically calibrating the image of berries can comprise a reference object of known dimensions.

The device according to the invention can also comprise means for correcting the colours of the image of berries. These means for correcting the colours of the image of berries can comprise a colour test pattern. In a first embodiment, the test pattern is a black and white bi-coloured circular test pattern. In a second embodiment, the test pattern is a "Macbeth"-type colour test pattern.

The means for determining geometric and/or colorimetric characteristics can comprise image-processing means, such as a computer and image processing software.

The device according to the invention can also comprise means for accessing a database comprising in particular other results of berry analyses obtained using any device. These analysis results can therefore be both geometric and/or colorimetric characteristics obtained using a device according to the invention, and other types of data such as sugar assays.

The device according to the invention can also comprise means for visualizing the determined geometric and/or colorimetric characteristics and/or other data. It can also moreover comprise means for visualizing a development over time of geometric and/or colorimetric characteristics determined according to the invention and/or of other data.

The device according to the invention can also comprise means for exporting, to a spreadsheet file, geometric and/or colorimetric characteristics, and/or other results of berry analyses obtained using any device. In a preferential embodiment, the file is an Excel file.

DESCRIPTION OF THE FIGURES AND EMBODIMENTS

Figure 2:
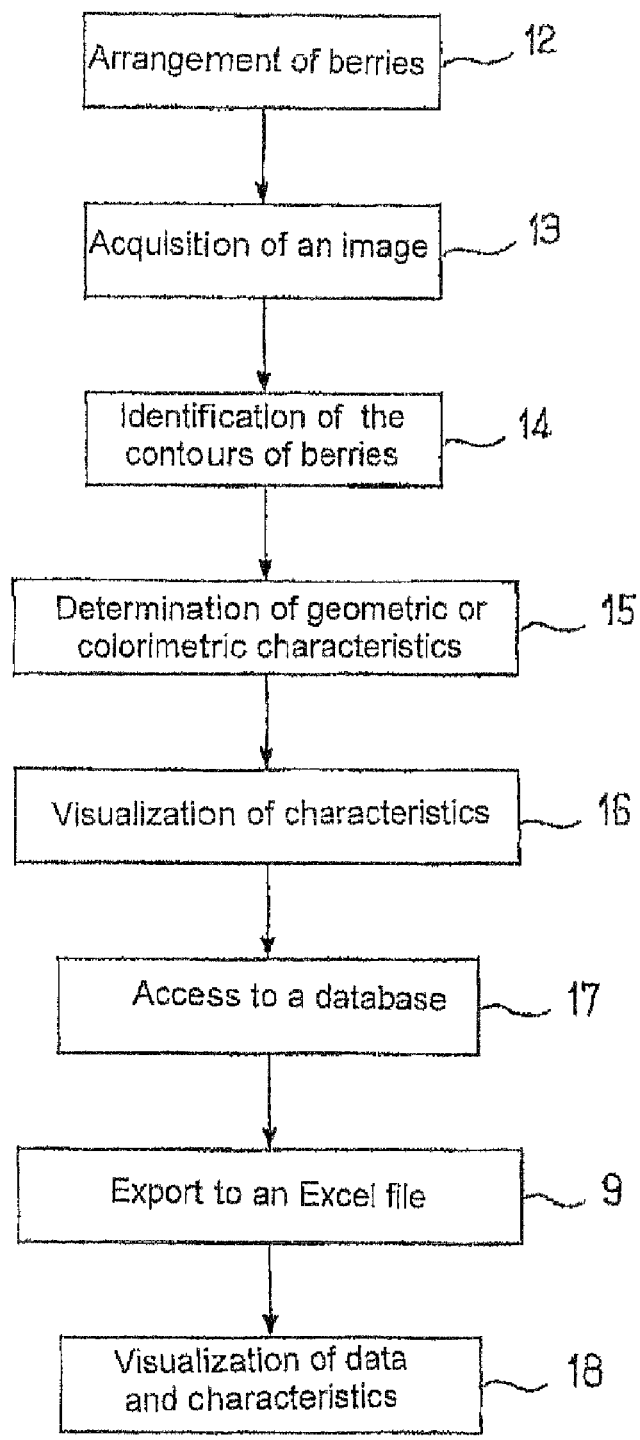
Figure 3A:
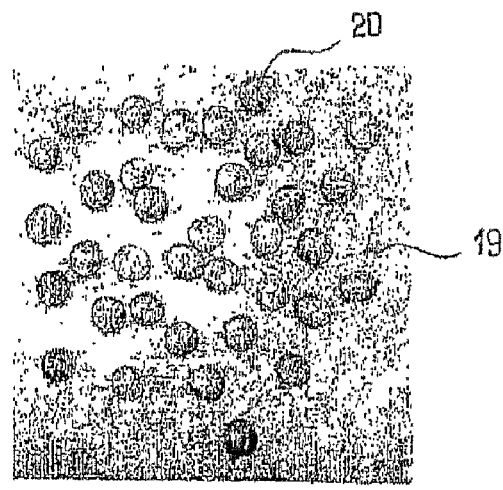
Figure 3B:
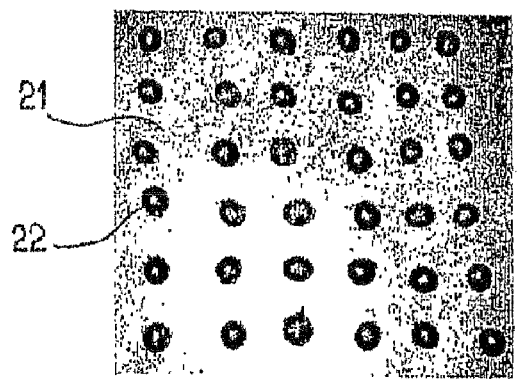
Figure 4A:
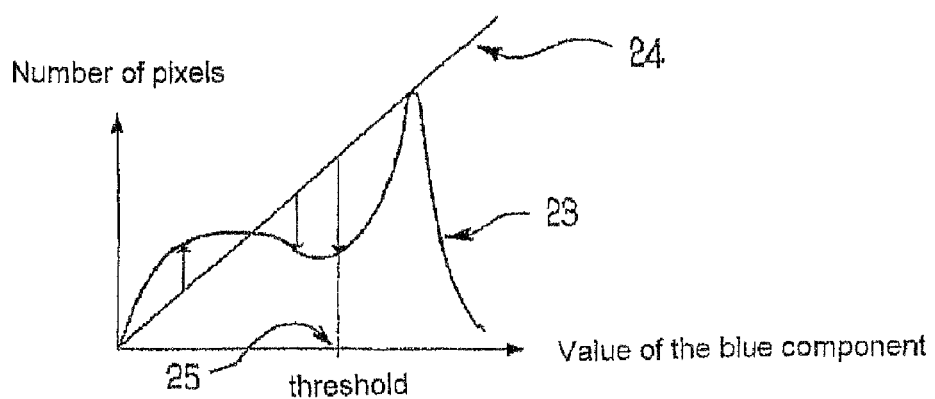
Figure 4B:
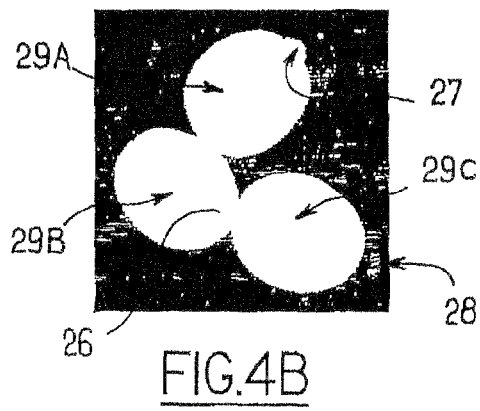
Figure 4E:
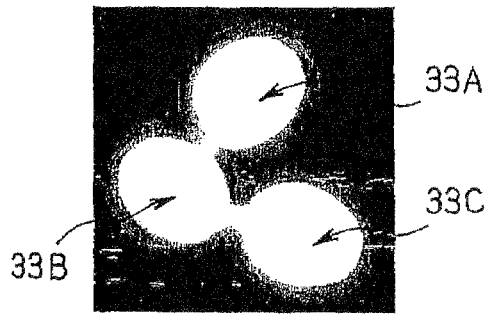
Figure 4C:
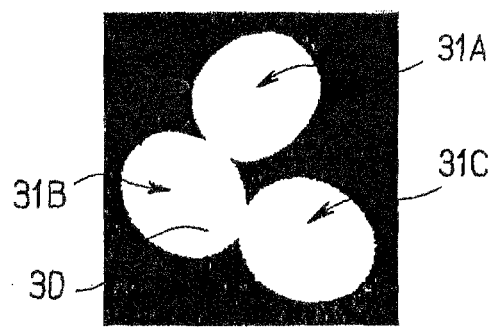
Figure 4F:
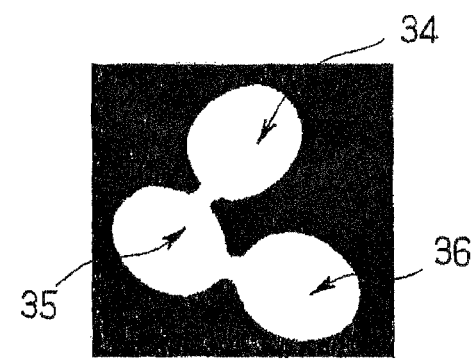
Figure 4D:
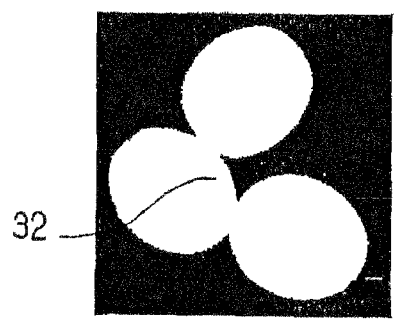
Figure 4G:
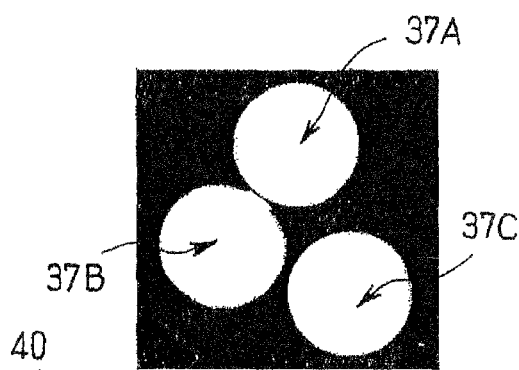
Figure 4H:
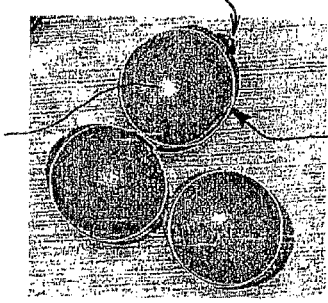
Figure 5:
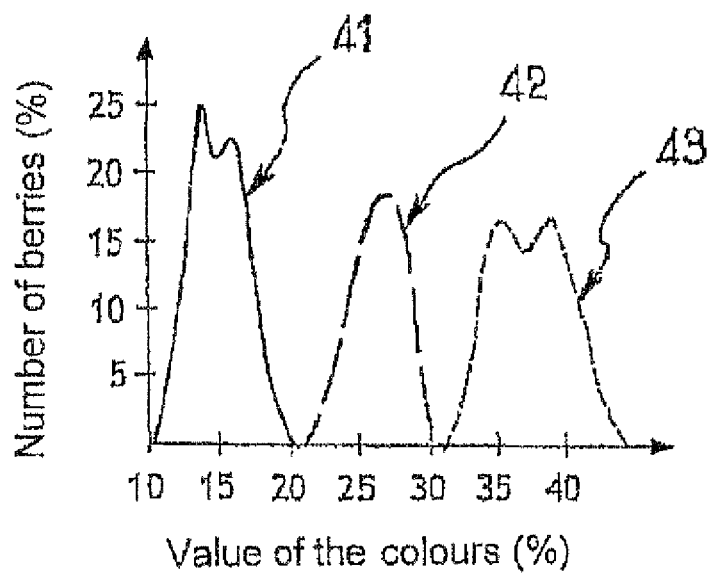
Figure 6:
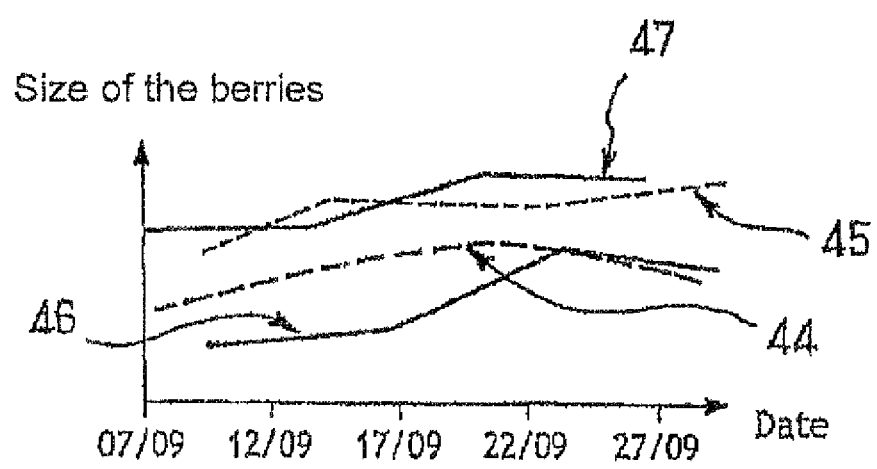

Other advantages and characteristics of the invention will become apparent on examination of the detailed description of embodiments which are in no way limitative, and the attached diagrams, in which:

FIGS. 1A and 1B illustrate a device for analyzing berries according to the invention, FIG. 2 is a flowchart of an implementation of the method according to the invention, FIG. 3A illustrates an image of berries arranged on an analysis plate in a random manner, and acquired using a device according to the invention, FIG. 3B illustrates an image of berries arranged on an analysis plate in ordered manner, and acquired using a device according to the invention, FIGS. 4A to 4H illustrate an identification of contours of berries in an image according to the invention:

FIG. 4A illustrates a method of calculating a threshold for the value of a colour component, FIG. 4B illustrates a conversion of an image of berries to a thresholded image, FIG. 4C illustrates a deletion of small impurities from a thresholded image, FIG. 4D illustrates a deletion of impurities of a luminous reflection type from a thresholded image, FIG. 4E illustrates a conversion of a thresholded image to a grey-scale image, FIG. 4F illustrates a thresholding of a grey-scale image by fuzzy logic, FIG. 4G illustrates an image berry by berry, FIG. 4H illustrates a digital image of a berry with the contour defined, FIG. 5 illustrates a visualization of characteristics of berries determined according to the invention, and FIG. 6 illustrates a visualization of the development of a characteristic of berries determined according to the invention, as a function of time.

Firstly a description will be given, with reference to FIGS. 1A and 1B, of an example of a device 1 for analyzing berries according to the invention. FIG. 1A is a general view and FIG. 1B is a cross-sectional side view of the device 1. Such a device comprises a berry analysis plate 2, on which berries can be arranged. It also comprises under its top part 3 means 4 for lighting berries arranged on the plate comprising a circular neon tube, and means 5 for the acquisition of a digital image, approximately focussed on the analysis plate. It also comprises a PC panel 6 comprising a computer central processing unit, an image processing software which makes it possible to extract from a digital image of berries geometric and/or colorimetric characteristics of said berries, means for connection to a database, and a visualization touch-screen 8. The visualization screen makes it possible in particular to visualize the extracted geometric and/or colorimetric characteristics, or other data, such as developments over time of geometric and/or colorimetric characteristics determined according to the invention, or data originating from a database or of any other source. It also allows interaction with a user.

The device 1 also comprises a ground glass 7 between the lighting means 4 and the plate 2, in order to homogenize the light at the level of the plate.

The analysis plate 2 can have spaced recesses on its surface.

In a preferential embodiment, the analysis plate 2 is of a colour distinct from the colour of the berries, for example blue in the case of grape berries.

Such a device can also comprise means 10 for correcting the colours of the digital image or means 11 for geometrically calibrating the image. In order to correct the colours, it is possible for example to envisage a black and white circular two-tone test pattern situated on the plate 2. This test pattern, especially designed for calibrating the systems restoring the colour, is constituted by a white disc on a black disc twice as large, with the known proportions of elementary colours red, green, and blue. It would also be possible to envisage a "Macbeth"-type test pattern situated on the plate 2. This test pattern, also designed for calibrating the systems restoring the colour, is constituted by a plurality of boxes of different colours, with the known proportions of elementary colours red, green, and blue. In order to geometrically calibrate the image, it is possible to use a reference object of known dimensions, such as a graduated test pattern. It is however sensible to use the positioning plate 2 as reference object with known dimensions.

The geometric calibration is necessary in order to know the size of a pixel of an image in millimeters, which is useful during calculation of a berry's volume. The means 10 for correcting the colours and the means 11 for geometrically calibrating the image are not however necessary in the case where the lighting means 4, as well as the relative position of the lighting means 4 with respect to the plate 2, do not change, as in this case the device can be calibrated only once during its manufacture.

We shall now describe, with reference to FIG. 2, a flowchart of an implementation of the berry analysis method according to the invention. The method commences with an arrangement 12 of the berries on an analysis plate. An acquisition 13 is then made of an image of the berries on the plate, succeeded by an identification 14 of the contours of the berries present in the image. The image is composed of pixels of a plurality of elementary colour components, in a standard fashion red, green and blue. An example of identification of contours is shown in detail in the following figures. This identification of contours allows a determination 15 of geometric and/or colorimetric characteristics, such as:

characteristic radii or a perimeter for each berry,
a volume for each berry,
an average and a heterogeneity factor of the volume of all the berries,
a surface area for each berry,
an average and a heterogeneity factor of the surface area of all the berries,
a surface area to volume ratio for each berry,
an average and a heterogeneity factor of the surface area to volume ratio of all the berries,
an average, for all the pixels inside the contour of a considered berry, of the values of a considered elementary colour component, and
an average, for all the pixels inside the contour of a considered berry, of the values of a considered colour component of interest.
an average and a heterogeneity factor of the averages of the values of an elementary colour component or of a colour component of interest of all the berries.

By heterogeneity factor may be meant a dispersion coefficient calculated by a standard deviation to average ratio.

During the determination of the contour of each berry, each berry is labelled, and the number of berries is thus also determined.

Determination of the geometric and/or colorimetric characteristics of the berries can be followed by the visualization 16 of these characteristics. This visualization can comprise the display of statistics of the determined characteristics on the analyzed berries. These statistics can comprise curves, histograms, or values such as averages or heterogeneity factors.

Access 17 to a database makes it possible moreover to save the determined characteristics, and to compare these characteristics with data originating from other analyses:

carried out according to a method according to the invention or according to any method such as for example a chemical assay of sugars,
carried out on the same day or not,
carried out on berries originating from the same plot or not,
carried out on berries from the same type of vine or not,
carried out on behalf of the same customer or not,
carried out on berries originating from a plot belonging to the same structure or not, Export 9 to a spreadsheet file such as Excel makes it possible to save characteristics determined according to the invention and/or the results of analysis of berries obtained by any methods, and thus makes it possible to work on these data in an external system.

A visualization 18 makes it possible to study, correlate, compare or monitor all these data and characteristics over time.

The method according to the invention can also comprise a geometric calibration of the image or a correction of the colours of the image.

FIG. 3A illustrates an image of berries 20 arranged on an analysis plate 19 in random manner, and acquired using a device according to the invention. The image is acquired in digital format, and possesses pixels of three elementary colour components: red, green and blue.

FIG. 3B illustrates an image of berries 22 arranged on an analysis plate 21 in ordered manner, and acquired using a device according to the invention. This analysis plate 21 possesses spaced recesses on its surface, which makes it possible to easily arrange the grape berries in an ordered manner. The image is acquired in digital format, and possesses pixels of three elementary colour components: red, green and blue. The berries are arranged in a regular manner horizontally and vertically, thus forming a sort of grid of berries.

We shall now describe, with reference to FIGS. 4A, 4B, 4C, 4D, 4E, 4F, 4G and 4H, an identification of contours of berries in an image according to the invention, applied to the particular case of white grape berries and of a digital image composed of pixels of three elementary colour components: red, green and blue.

After having acquired a digital image such as those illustrated in FIG. 3A or 3B, the digital image is first thresholded. The thresholding is carried out according to a certain threshold for a value of an elementary colour component. In the particular case of grape berries, it is sensible to use a blue analysis plate distinct from the berries. In this case, the thresholding is carried out according to a certain threshold for a value of the blue component.

FIG. 4A illustrates a graphic explanation of a method for the calculation of such a threshold for a value of the blue component. The curve 23 of the number of pixels as a function of the value of the blue component of said pixels is traced, as well as the straight line 24 passing through the maximum of the curve 23 and through the origin. The threshold 25 corresponds to the value for which the vertical distance between the straight line 24 and the curve 23 is greatest.

Once the threshold is determined, the digital image is thresholded: if the blue component of a pixel of the digital image is greater than or equal to the threshold, the corresponding pixel in the thresholded image is set to 0, otherwise it is set to 1. A thresholded image is then obtained in which several berries appear in blocks or are separated. FIG. 4B illustrates a thresholded image, in which a block 26 of three berries can be distinguished. This thresholded image is a fragment of an image comprising numerous berries which are isolated or in blocks. Moreover it is possible to distinguish small impurities 28 outside the block 26, impurities 29A, 29B and 29C inside the block 26 due to lighting reflections on the berries, and a large impurity 27 originating from the stalk of a berry. In order to delimit distinctly and precisely the contour of the berries in the thresholded image, it remains to eliminate the impurities from the thresholded image, and to separate the blocks of berries.

In order to eliminate the small impurities and the stalks, an opening operator from mathematical morphology is used, comprising a set of an erosion followed by a dilation, reiterated several times. FIG. 4C illustrates the result of such an operator applied to the thresholded image of FIG. 4B. A block of berries 30 can still be distinguished there, as well as impurities 31A, 31B and 31C inside the block 30 due to lighting reflections on the berries.

In order to eliminate the impurities inside the block of berries, an algorithm for filling holes by propagation is used. FIG. 4D illustrates the result of such an algorithm applied to the thresholded image of FIG. 4C. A block 32 of three berries can still be distinguished there, which remain to be separated.

In order to separate the berries, the thresholded image of FIG. 4D is first converted to a grey-scale image for which each pixel has as its value the number of pixels of the thresholded image not belonging to the analysis plate on a circle centred on the corresponding pixel of the thresholded image. Typically, this circle has a parametrable radius the default value of which is approximately one-hundredth of the size of the block of berries. FIG. 4E illustrates such a grey-scale image obtained from the thresholded image of FIG. 4D. It is possible to distinguish therein a grey-scale block of three berries comprising three lobes 33A, 33B and 33C. A thresholding of the grey-scale image is then carried out by fuzzy logic. FIG. 4F illustrates the result of such thresholding, obtained from the grey-scale image of FIG. 4E. It is possible to distinguish in FIG. 4F three lobes 34, 35 and 36, i.e. one lobe per berry. An erosion operator from mathematical morphology is then used on the image obtained in order to calculate a final erosion, and thus obtain the centre of gravity of each berry, which makes it possible to label each berry and to calculate a bounding box for each berry. Finally, by extension around the centres of gravity of each berry and by layer effect with the starting thresholded image illustrated in FIG. 4B, a "berry by berry image" is obtained, in which it is possible to distinguish the contour of each berry. FIG. 4G illustrates a "berry by berry image" obtained from the image illustrated in FIG. 4F. It is possible to distinguish in FIG. 4G three distinct berry shapes 37A, 37B and 37C.

The previously determined contour of each berry is then superimposed on the digital image which has been acquired. Then a colour digital image is obtained in which the contour of each berry is determined. FIG. 4H is a fragment of such a colour digital image, in which it is possible to distinguish in particular a berry 38, its contour 39, and its stalk 40 outside its contour, among a group of three berries.

It should be noted that in the case where the berries are arranged in an ordered manner on an analysis plate, this avoids having to separate blocks of berries into clearly distinct berries.

It is possible to apply an identification of contours of berries according to the invention to an image comprising hundreds of berries in blocks or isolated. It is then possible to determine geometric characteristics such as:
  characteristic radii or a perimeter for each berry,
  a volume V for each berry. It is possible for example to use the formula:

$$V = \frac{4}{3}\pi R r^2$$

with r the shortest distance between the centre of gravity and the contour of the berry, and R the longest distance between the centre of gravity and the contour of the berry,
  an average and a heterogeneity factor of the volume of all the berries,
  a surface area S for each berry. By surface area is meant the surface of the berry in space, and not the surface inside the contour of the berry and contained in the plane of the digital image. It is possible for example to use the formula:

$$S = \pi\left(2r^2 + \frac{R^2}{\sqrt{1-\frac{r^2}{R^2}}}\ln\left(\frac{1+\sqrt{1-\frac{r^2}{R_2}}}{1-\sqrt{1-\frac{r^2}{R_2}}}\right)\right)$$

with r the shortest distance between the centre of gravity and the contour of the berry, and R the longest distance between the centre of gravity and the contour of the berry,
  an average and a heterogeneity factor of the surface area of all the berries,
  a surface area to volume ratio for each berry, and
  an average and a heterogeneity factor of the surface area to volume ratio of all the berries.

Since it is possible to determine these characteristics for all the berries of the image, it is obviously possible to determine the number of berries. It should moreover be noted that the acquisition of an image in black and white is sufficient for the determination of the geometric characteristics listed previously.

In the case where an acquisition has been made of a digital image, composed of pixels of three elementary colour components red, green and blue, it is also possible to determine colorimetric characteristics such as:
  an average, for all the pixels inside the contour of a considered berry, of the values of the red elementary component, an average, for all the pixels inside the contour of a considered berry, of the values of the green elementary component, an average for all the pixels inside the contour of a considered berry, of the values of the blue elementary component, an average, for all the pixels inside the contour of a considered berry, of the values of a colour component of interest, and an average and a heterogeneity factor of the averages of the values of an elementary colour component or of a colour component of interest of all the berries.

In the case of an analysis of white grape berries, yellow and green are particularly relevant colours of interest. In fact, as it matures, a white grape berry has a tendency to become golden, passing from green to yellow. Analysis of these two colours can then provide information on the maturity of the white grape berries.

In the case of the analysis of red grape berries, red and black are particularly relevant colours of interest. In fact, as it matures, a red grape berry has a tendency to become darker. Analysis of these two colours can then provide information on the maturity of the red grape berries.

In the case where an acquisition has been made of an image of berries one elementary colour component of which is situated in the infrared, it is also possible to determine a colorimetric characteristic such as an average, for all the pixels inside the contour of a considered berry, of the values of the colour component in the infrared. It is than possible to deduce from this, by infrared spectrophotometry and chemometry, characteristic concentrations for each berry, as well as an average and a heterogeneity factor of at least one characteristic concentration of all the berries. The characteristic concentrations can for example consist of a quantity of sugar, an acidity, a nitrogen concentration, an anthocyanin concentration, or a polyphenol concentration.

FIG. 5 illustrates a visualization of characteristics of berries determined according to the invention, from a digital image composed of pixels of three components of elementary colours red, green and blue, of white grape berries. Y represents the number of berries, as a percentage, as a function of the average per berry of the values of the red (dashed curve 42), green (dotted curve 43), and blue (unbroken curve 41) elementary colour component. It would similarly be possible to plot the number of berries, as a percentage, as a function of any of the geometric and/or colorimetric characteristics listed in the preceding paragraphs. Access to a database makes it possible to save determined characteristics. This access makes it possible for example to monitor the development over time of these characteristics by carrying out the method according to the invention several times, spaced out over time. This access also makes it possible to correlate these characteristics with data originating from other analyses such as a sugar assay.

FIG. 6 illustrates a visualization of a characteristic of berries, the average volume of the berries, determined according to the invention, as a function of time. It is possible to distinguish 4 curves 44, 45, 46, and 47, representing the average volume of the berries from four different plots of white grapes, between 7th September and 30th September. As in the case of FIG. 5, it would be possible to trace the development over time of any other determined geometric or colorimetric characteristic. One of the most relevant data is in particular the ratio between the surface area and the volume of the berries.

Of course, the invention is not limited to the examples which have just been described and numerous adjustments can be made to these examples without exceeding the scope of the invention. In particular, it is possible to envisage numerous variations with regard to the manner of identifying the contours of the berries.

The invention claimed is:

1. A method for analyzing berries, comprising:
   arranging berries on an analysis plate;
   an acquisition of an image of the arranged berries, said image of the berries being composed of pixels of at least one elementary colour component;
   an identification, by a processor, of contours of the berries;
   a determination, by the processor, of geometric or colorimetric characteristics of the berries;
   a reiteration of the method according to the invention on a same type of berry over an extended period of time, and a monitoring over the extended period of time of one of the geometric and colorimetric characteristics determined on the berries of the same type to represent capture and analysis of variation of the determined geometric or colorimetric characteristic values of the berries over the extended period of time; and
   a visualisation, on a visualization screen, of a graph illustrating development over the extended period of time of the determined geometric or colorimetric characteristics.

2. The method according to claim 1, further comprises saving at least one of the determined characteristics.

3. The method according to claim 1, wherein the berries of the same type originate from a same plot.

4. The method according to claim 1, further comprises a visualisation of determined characteristics.

5. The method according to claim 1, further comprises a determination of the number of berries in the image of berries.

6. The method according to claim 1, wherein the determination of characteristics comprises a determination of a volume per berry.

7. The method according to claim 1, wherein the determination of characteristics comprises a determination of a surface area per berry.

8. The method according to claim 1, wherein the determination of characteristics comprises a determination of a surface area to volume ratio per berry.

9. The method according to claim 1, wherein the determination of characteristics comprises, for each berry and at least one of the elementary colour components or a colour component of interest, a calculation of an average, for all the pixels of the image of berries inside the contour of a berry, of the values of the considered colour component.

10. The method according to claim 1, wherein the determination of characteristics comprises a calculation of a heterogeneity factor and an average of a determined characteristic for each berry.

11. The method according to claim 1, further comprises a lighting of the berries according to predetermined lighting conditions.

12. The method according to claim 1, further comprises a geometric calibration of the image of the berries.

13. The method according to claim 1, further comprises a correction of the colours of the image of the berries.

14. The method according to claim 1, wherein the monitoring over the extended period of time of at least one of the geometric or colorimetric characteristics determined on the berries of the same type occurs under substantially similar lighting conditions.

15. The method according to claim 9, wherein the method is applied to white grape berries, and in that the considered colour component is yellow or green, or in that it is applied to red grape berries, and in that the considered colour component is red or black.

16. The method according to claim 9, wherein the elementary colour component is situated in the infrared, and in that it also comprises a determination, by infrared spectrophotometry and chemometry, of at least one characteristic concentration per berry.

17. The method according to claim 1, wherein the identification of contours of the berries comprises:
   a conversion of the image of the berries to a thresholded image, in which it is possible to distinguish blocks of berries,
   a deletion of impurities from the thresholded image, and
   a segmentation of the blocks of berries to berries with defined contours.

18. The method according to claim 17, wherein the conversion to a thresholded image comprises a thresholding of the image of the berries according to a threshold for a value of an elementary colour component.

19. The method according to claim 17, wherein the deletion of impurities comprises a succession of erosions and dilations of the blocks of berries.

20. The method according to claim 17, wherein the deletion of impurities comprises an algorithm for filling holes by propagation.

21. The method according to claim 17, wherein the segmentation of the blocks of berries comprises:
   a conversion of the thresholded image to a grey-scale image,
   a thresholding of the grey-scale image by fuzzy logic,
   a use of an erosion operator until a centre of gravity for each berry is obtained, and
   an expansion around the centres of gravity, until the contours of the berries are obtained.

22. The method according to claim 1, further comprises an access to a database comprising at least one result of another analysis of berries obtained using any method.

23. The method according to claim 22, wherein the analysis result consists of a concentration.

24. The method according to claim 22, further comprises obtaining an item of data by matching at least one of the determined characteristics with the analysis result of berries obtained using any method.

25. The method according to claim 24, wherein the determination of characteristics comprises a determination of an average volume of the arranged berries, and in that it comprises obtaining a sugar content by matching the determined volume and a concentration of sugars.

26. A device for analyzing berries implementing a method according to claim 1, comprising:
   an analysis plate;
   means for acquiring an image of berries arranged on the analysis plate, said image being composed of pixels of at least one elementary colour component;
   means for determining geometric or colorimetric characteristics of the berries;
   a means for carrying out a monitoring over an extended period of time of at least one of the determined characteristics on berries of the same type to represent capture and analysis of variation of the determined geometric or colorimetric characteristic values of the berries over the extended period of time; and
   a visualization screen for visualizing a graph illustrating a development over the extended period of time of at least one of the determined geometric or colorimetric characteristics.

27. The device according to claim 26, further comprises means for saving at least one of the determined characteristics.

28. The device according to claim 26, further comprises means for visualizing at least one of the determined characteristics.

29. The device according to claim 26, wherein the analysis plate comprises spaced recesses.

30. The device according to claim 26, wherein the means for acquiring an image of berries comprise a multispectral camera carrying out an acquisition of an image of berries in a visible range or an infrared range.

31. The device according to claim 26, wherein the means for determining geometric or colorimetric characteristics include image-processing means.

32. The device according to claim 26, further comprises means for accessing a database comprising at least one result of another analysis of berries obtained using any device.

33. The device according to claim 32, further comprises means for obtaining an item of data by matching at least one of the determined characteristics with the result of analysis of berries obtained using any device.

34. The device according to claim 26, further comprises means for lighting berries arranged on the analysis plate.

35. The device according to claim 34, further comprises a ground glass surface situated between the lighting means and the analysis plate, and situated upstream of the means for acquiring an image of berries.

36. The device according to claim 26, further comprises means for geometrically calibrating the image of the berries.

37. The device according to claim 36, wherein the means for geometrically calibrating the image of berries include a reference object of known dimensions.

38. The device according to claim 26, further comprises means for correcting the colours of the image of berries.

39. The device according to claim 38, wherein the means for correcting the colours of the image of berries include a colour test pattern.

* * * * *

UNITED STATES PATENT AND TRADEMARK OFFICE
CERTIFICATE OF CORRECTION

PATENT NO. : 8,406,475 B2  Page 1 of 1
APPLICATION NO. : 11/994120
DATED : March 26, 2013
INVENTOR(S) : Bernard et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1438 days.

Signed and Sealed this
First Day of September, 2015

Michelle K. Lee
*Director of the United States Patent and Trademark Office*